(12) United States Patent
Pavesio et al.

(10) Patent No.: US 6,872,819 B1
(45) Date of Patent: Mar. 29, 2005

(54) BIOMATERIALS CONTAINING HYALURONIC ACID DERIVATIVES IN THE FORM OF THREE-DIMENSIONAL STRUCTURES FREE FROM CELLULAR COMPONENTS OR PRODUCTS THEREOF FOR THE IN VIVO REGENERATION OF TISSUE CELLS

(75) Inventors: Alessandra Pavesio, Padua (IT); Massimo Dona', Due Carrare (IT); Lanfranco Callegaro, Thiene (IT)

(73) Assignee: Fidia Advanced Biopolymers S.r.l., Brindisi (IT)

( * ) Notice: Subject to any disclaimer, the term of this patent is extended or adjusted under 35 U.S.C. 154(b) by 0 days.

(21) Appl. No.: 09/700,142

(22) PCT Filed: May 27, 1998

(86) PCT No.: PCT/EP99/03604

§ 371 (c)(1),
(2), (4) Date: Nov. 9, 2000

(87) PCT Pub. No.: WO99/61080

PCT Pub. Date: Dec. 2, 1999

(30) Foreign Application Priority Data

May 27, 1998 (IT) .......................................... PD98A0131
Dec. 21, 1998 (IT) .......................................... PD98A0299

(51) Int. Cl.$^7$ ............................................. C08B 37/00
(52) U.S. Cl. .................. 536/55.3; 536/123.1; 536/55.1; 536/55.2; 536/55; 428/401; 428/427; 428/422; 428/423; 514/54
(58) Field of Search ............................. 536/55.3, 55.1, 536/55.2, 123.1, 55; 428/401, 427, 422, 423; 514/54

(56) References Cited

U.S. PATENT DOCUMENTS

| | | | |
|---|---|---|---|
| 4,851,521 A | 7/1989 | della Valle et al. | ......... 536/55.1 |
| 5,646,129 A | 7/1997 | Callegaro et al. | ............. 514/54 |
| 5,676,964 A | 10/1997 | Della Valle et al. | ........ 424/423 |
| 6,509,322 B2 * | 1/2003 | Benedetti et al. | ............. 514/54 |

FOREIGN PATENT DOCUMENTS

| | | |
|---|---|---|
| EP | 0216453 | 4/1987 |
| EP | 0138572 | 7/1990 |
| IT | WO 93/11803 A1 * | 6/1993 |
| WO | WO9311803 | 6/1993 |
| WO | WO9525751 | 9/1995 |
| WO | WO9633750 | 10/1996 |
| WO | WO9718842 | 5/1997 |
| WO | WO9856897 | 12/1998 |

OTHER PUBLICATIONS

Biomaterials, 20 (1999) 1097–1108, "An Osteoconductive Collagen/hyaluronate matrix for bone regeneration", Lin–Shu Liu, et al.
"Cartilage tissue engineering with novel nonwoven structures biomaterial based on hyaluronic acid benzyl ester", J. Aigner et al. (1998).
Abstract, WO9218542, "Procedure for the Purification of Hyaluronic Acid and Fraction of Pure Hyaluronic Acid for Ophthalmic Use", Romeo Aurelio et al., Oct. 29, 1992.
J. Theor, Biol. (1986) 119, 219–234, "A Model for the Role of Hyaluronic Acid and Fibrin in the Early Events during the Inflammatory Response and Wound Healing", Paul H. Weigel et al.
Abstract, U.S. 4,965,353, della Valle Francesco et al.
Abstract, PCT WO 9320858, Oct. 28, 1993, Callergaro et al., "Biomaterials for Bone Replacements".
Abstract, U.S. 5,520,916, May 28, 1996, Callegaro et al., "Non–Woven Fabric Material Comprising Hyaluronic acid Derivatives".

* cited by examiner

Primary Examiner—Dwayne Jones
(74) Attorney, Agent, or Firm—Hedman & Costigan, P.C.

(57) ABSTRACT

Biomaterials are disclosed comprised of biodegradable, biocompatible, and bioabsorbable non-woven fabric materials for use in surgery for the guided regeneration of tissues. The non-woven fabric materials are comprised of threads embedded in a matrix, wherein both the matrix and the threads can be comprised of esters of hyaluronic acid, used singly or in combination, or esters of hyaluronic acid in combination with esters of alginic acid or other polymers.

7 Claims, 3 Drawing Sheets

US 6,872,819 B1

BIOMATERIALS CONTAINING HYALURONIC ACID DERIVATIVES IN THE FORM OF THREE-DIMENSIONAL STRUCTURES FREE FROM CELLULAR COMPONENTS OR PRODUCTS THEREOF FOR THE IN VIVO REGENERATION OF TISSUE CELLS

This application is a 371 of PCT/EP99/03604 filed on May 25, 1999.

FIELD OF THE INVENTION

The present invention relates to the use of hyaluronic acid derivatives, with three-dimensional structures enclosing hollow spaces created by communicating pores and/or entangled fine, fibres or microfibres, for the preparation of biocompatible biomaterials for in vivo regeneration of tissue cells, characterised in that said biocompatible biomaterials are free from cellular components or products thereof, and more in particular to a method for regenerating a mammal human tissue comprising applying in vivo to the site requiring such a treatment these biocompatible biomaterials.

BACKGROUND OF THE INVENTION

Hyaluronic acid is a polysaccharide ether composed of alternate residues of D-glucuronic acid and N-acetyl-D.glycosamine. It is a straight-chained polymer with a molecular weight varying between 50,000 and 13,000,000 Da, depending on the source from which it is obtained and the methods of preparation and determination used. It is present in nature in pericellular gels, in the fundamental substance of the connective tissue of vertebrate organisms, of which it is one of the main components, in the synovial fluid of joints, in the vitreous humor, in human umbilical cord and in rooster combs.

Hyaluronic acid plays a vital role in many biological processes such as tissue hydration, proteoglycan organisation, cell differentiation, proliferation and angiogenesis (J. Aigner et al., L. Biomed. Mater. Res. 1998, 42, 172–181).

It is well known that fractions of hyaluronic acid can be used to facilitate tissue repair, as a substitute for the intraocular fluid, or administered by the intra-articular route to treat joint pathologies, as described in European patents Nos. 0138572 and 0535200.

Hyaluronic acid plays a fundamental role in the tissue repair process, especially in the first stages of granulation, stabilising the coagulation matrix and controlling its degradation, favouring the recruitment of inflammatory cells such as fibroblasts and endothelial cells and, lastly, orienting the subsequent migration of the epithelial cells.

It is known that the application of hyaluronic acid solutions can accelerate healing in patients affected by sores, wounds and burns. The role of hyaluronic acid in the various stages of the tissue repair process has been described by the construction of a theoretical model by P. H. Weigel et al.: "A model for the role of hyaluronic acid and fibrin in the early events during the inflammatory response and wound healing", J. Theor. Biol., 119: 219, 1986.

The use of low-molecular-weight hyaluronic acid fractions to prepare pharmaceutical compositions with osteoinductive properties is also known (U.S. Pat. No. 5,646,129).

Hyaluronic acid derivatives maintain all the properties of the abovesaid glycosaminoglycan with the advantage of being processable in various forms and having adaptable solubility and degradation times according to the type and percentage of the derivation (EP 0216453B1).

Moreover, hyaluronic acid derivatives have new properties resulting from the insertion of specific molecules in the structure of the hyaluronic acid, For example, the sulphated derivatives of hyaluronic acid present anticoagulant properties and are resistant to hyaluronidase (WO 95/25751).

The total or partial esters of hyaluronic acid and its cross-linked derivatives are also known, as is their use in the pharmaceutical and cosmetic fields and in that of biodegradable materials (U.S. Pat. Nos. 4,851,521, 4,965,353 and 5,676,964). Patent application No. WO 93/20858 describes binding solutions and pastes containing hyaluronic acid and/or its ester derivatives used as bone fillers in surgery.

Lastly, hyaluronic acid esters have been processed in the form of non-woven fabrics according to the process described in the U.S. Pat. No. 5,520,916.

The hyaluronic acid derivatives in a three dimensional form and in particular the hyaluronic partial and total esters processed as non woven tissue have been used as supports for the preparation of biological materials containing cellullar components and/or products generated by said cellular components.

For example we can mention:

WO96/33750 describing an artificial human skin comprising:
a) a microperforated membrane based on a hyaluronic acid derivative on which keratinocytes are seeded and cultured,
b) an underlying non woven tissue based on a hyaluronic acid derivative wherein fibroblasts have been seeded and left to proliferate;

WO 97/18842 describing a biologic material comprising:
a) an efficient culture of autologous or homologous bone marrow stem cells partially or completely differentiated into specific connective tissue cells, further comprising the extracellular matrix secreted by said cells, or alternatively
a') the extra cellular matrix secreted by completely or partially differentiate bone marrow stem cells or alternatively secreted by mature tissue cells.
b) a three dimensional matrix consisting of hyaluronic acid derivatives and in particular partial or total esters;

WO98/56897 dealing with a biological material comprising a three dimensional matrix of consisting of at least one derivative of hyaluronic acid on which endothelial, glandular cells are grown.

All these biomaterials, whose main use, in the field of graft surgery, require complex and long cultivation steps, before the same be transplanted in the site wherein tissue regeneration is required. In addition said materials containing cellular components require expensive stockage procedure such as cryopreservation. The biological material like that disclosed in WO 97/18842 containing only the extracellular matrix, requires besides the cellular cultivation also the step of cellular components removal.

The need is felt to dispose of a biocompatible biomaterial not showing the aforementioned drawbacks.

SUMMARY OF THE INVENTION

The Applicant has unexpectedly found that hyaluronic acid derivatives made in the form of three-dimensional structures, enclosing communicating hollow spaces created by pores and/or fine fibres or microfibres entangled together, in the absence of cellular components or products thereof, induce tissue regeneration that leads to the formation of a new tissue with the same structure and function as normal tissue, and being well integrated with the adjacent tissues also of different type.

In fact, said biomaterials present, surprisingly, an ability to create an extracellular environment similar to the embryonic one seen in mammal foetuses, and that stimulates tissue regeneration.

As hyaluronic acid derivatives become degraded they release oligomers, stimulate the recruitment of progenitor cells and favour development towards the cell lines of which the tissue in which the biomaterials are implanted is composed.

The structure of the biomaterials enclosing hollow spaces created by communicating pores and/or fine fibres or microfibres entangled together facilitates the penetration of host cells in the biomaterial, and their adhesion to the scaffold.

Moreover, said structure has properties of reabsorption that adapt to the dynamics of the regenerative processes.

The present invention therefore relates to the use of hyaluronic acid derivatives, with three-dimensional structures enclosing hollow spaces created by communicating pores and/or entangled fine, fibres or microfibres, for the preparation of biocompatible biomaterials for the in vivo regeneration of tissue cells characterised in that said biocompatible biomaterials are free from cellular components and/or products thereof.

The present invention further relates to a process for regenerating a tissue comprising applying in vivo to the site of the tissue to be regenerated, this biocompatible biomaterial.

The biocompatible biomaterials free from cellular components and containing the hyaluronic acid derivatives in the form of a three dimensional structures with communicating hollow spaces created by pores and/or fine fibres or microfibres entangled together are in particular able to regenerate tissues selected from epidermal, dermal, bone, cartilage, nerve, cardiovascular, adipose and hepatic tissues.

DETAILED DESCRIPTION OF THE INVENTION

Figure 1:
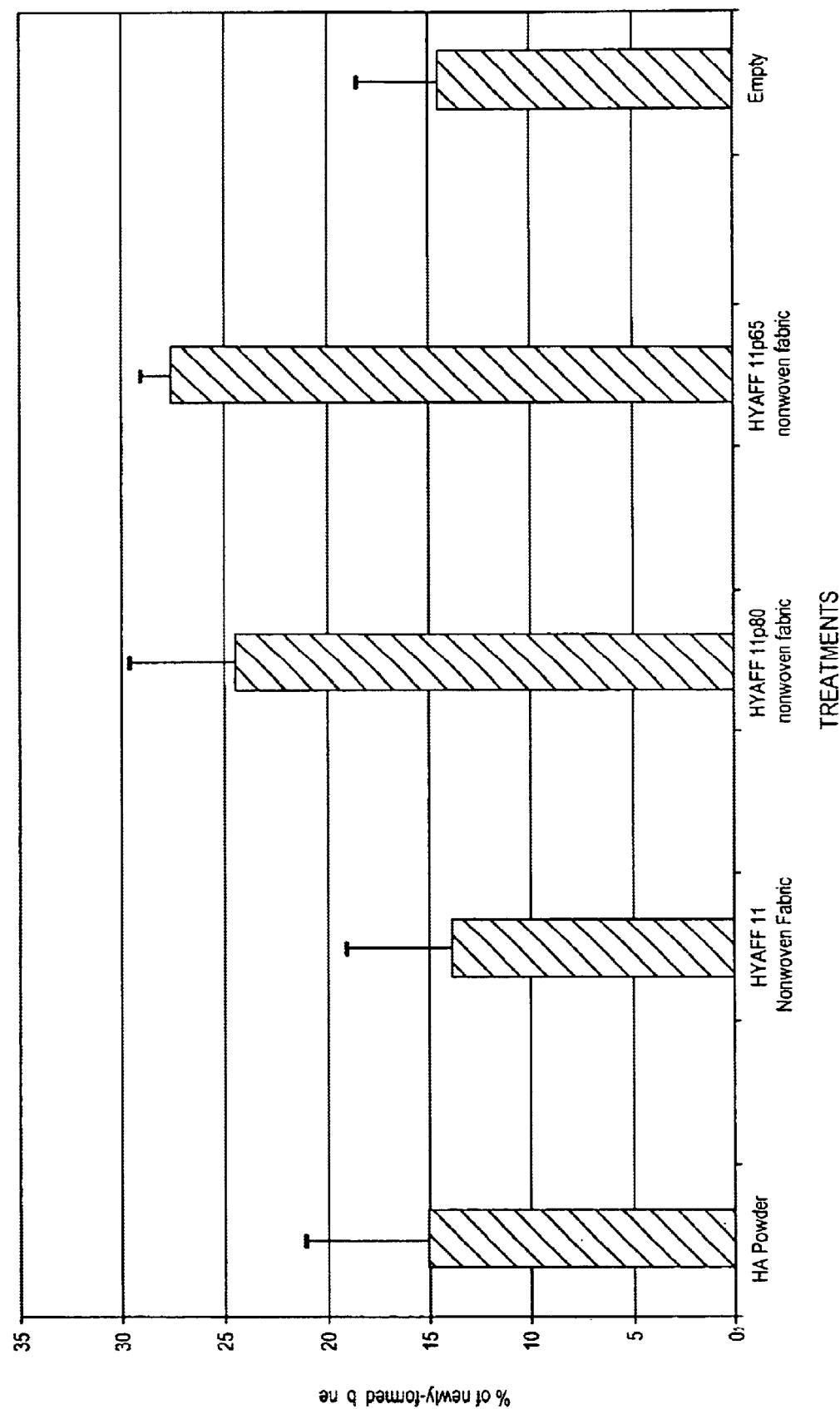
FIG. 1 reports the percentage of bone regeneration in a rat model, induced by hyaluronic acid in powder form and by benzyl esters of hyaluronic acid with varying percentages of esterification, in the form of fine fibres made into the form of non-woven fabrics at 24 days with the experiment as described in Example 1.
Figure 2:
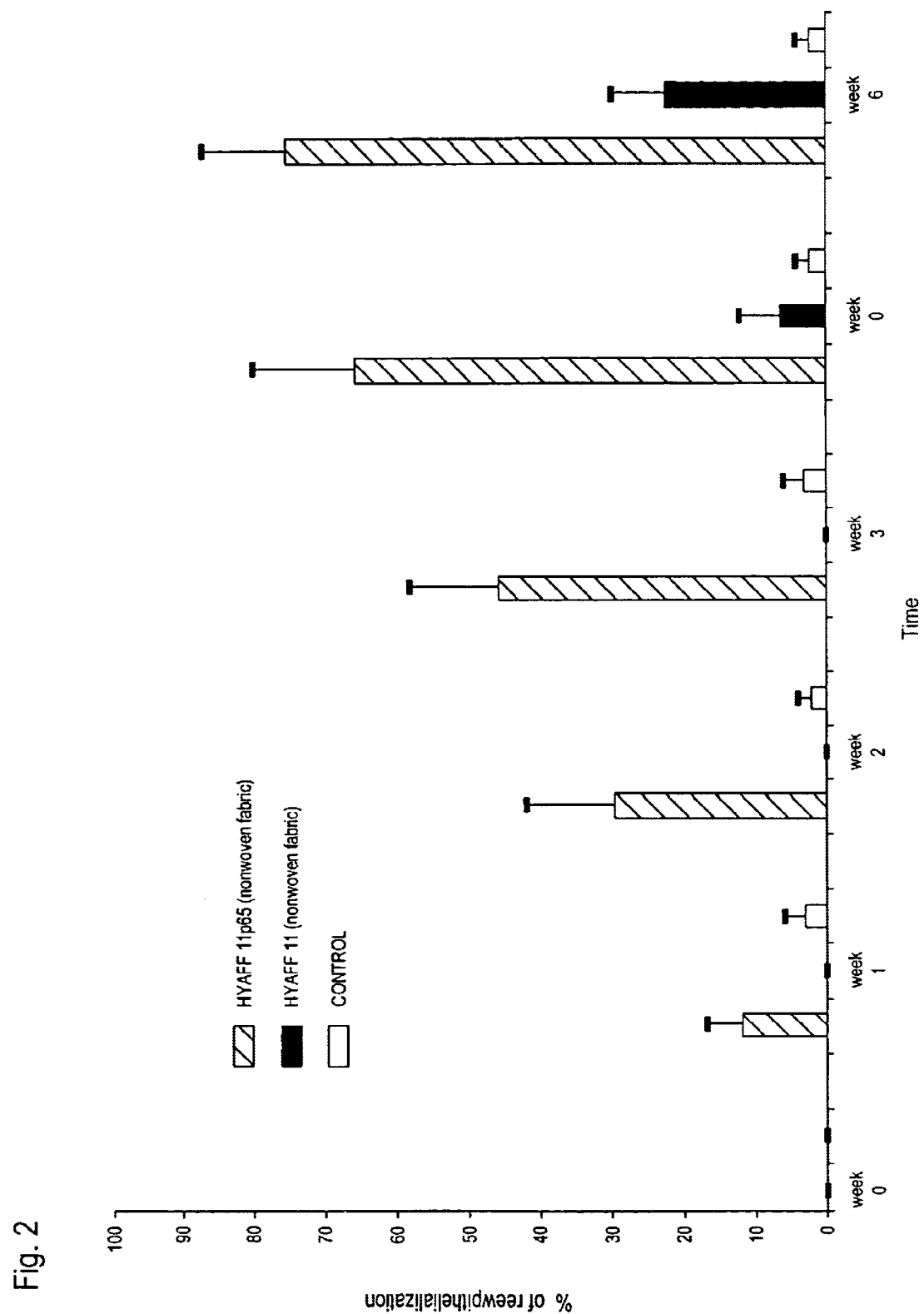
FIG. 2 reports the percentage of reepithelialization in a pig model using benzyl esters of hyaluronic acid with between 65 and 100% of esterification, in the form of fine fibres worked into the form of a non-woven fabric obtained with the experiment as disclosed in Example 2.
Figure 3:
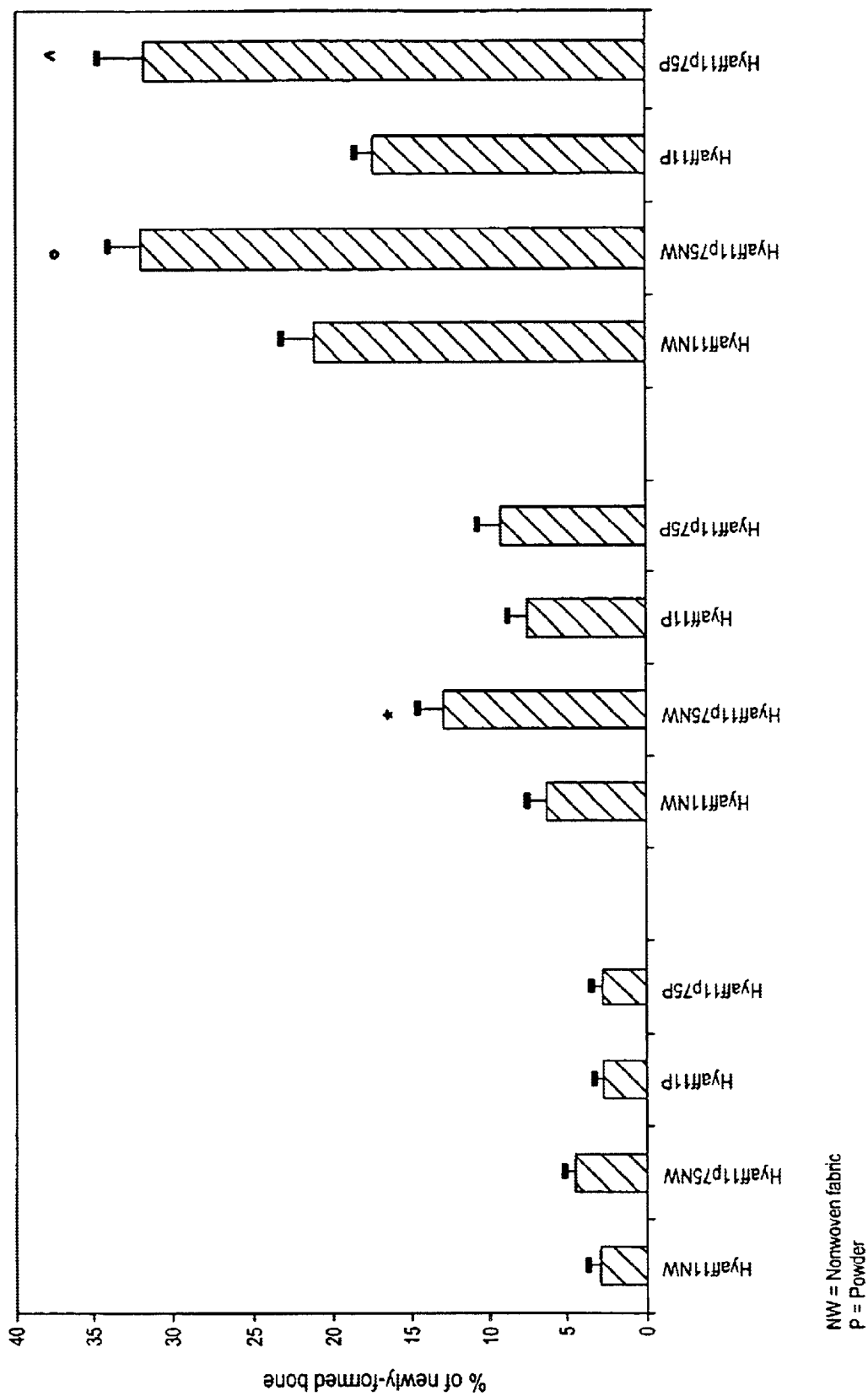
FIG. 3 reports the percentage of bone regeneration after an 8-mm lesion induced in rabbit calvaria, observed at 7–10 and 21 days obtained with the experiment described in Example 4, wherein:
*=P<0.05 HYAFF111 p75 NW vs HYAFF11 NW °=P<0.05 HYAFF11p75 NW vs HYAFF1 1 NW, HYAFF11P
^=P<0.05 HYAFF11p75 NW vs HYAFF11NW, HYAFF11P
NW=nonwoven
P=powder

The biocompatible biomaterial preferably contains in the form of three-dimensional structures with communicating hollow spaces created by pores and/or fine fibres or microfibres entangled together, at least one hyaluronic acid derivative selected from A) Esters of hyaluronic acid wherein part or all of the carboxy functions are esterified with alcohols of the aliphatic, aromatic, arylaliphatic, cycloaliphatic, heterocyclic series as disclosed in U.S. Pat. No. 4,851,521 we incorporate herewith by reference in its entirety;

B) The autocross-linked esters of hyaluronic acid wherein part or all of the carboxy groups are esterified with the alcoholic functions of the same polysaccharide chain or other chains as disclosed in U.S. Pat. No. 5,676,95 we incorporate herewith by reference in its entirety, C) The cross-linked esters of hyaluronic acid wherein part or all of the carboxy groups are esterified with polyalcohols of the aliphatic, aromatic, arylaliphatic, cycloaliphatic, heterocyclic series, generating cross-linking by means of spacer chains as described in U.S. Pat. No. 4,957,744 we incorporate herewith by reference;

D) The hemiesters of succinic acid or heavy metal salts of the hemiester of succinic acid with hyaluronic acid or with partial or total esters of hyaluronic acid as describe in WO 96/357207 we incorporate herewith by reference;

E) The sulphated derivatives (WO 95/25751) or N-sulphated derivatives (patent application No. WO 98/45335).

Particularly preferred are the biomaterials containing the partial esters of hyaluronic acid of type (A) aforementioned having an esterification degree lower than 85% and processed in the form of non woven tissue as disclosed in U.S. Pat. No. 5,520,916, we incorporate herewith by reference.

In fact said esters in the form of three-dimensional structures with communicating hollow spaces created by pores and/or fine fibres or microfibres entangled together present a surprising ability in the absence of cellular components or products thereof, to stimulate tissue regeneration which is greater than that obtained with percentages of esterification of over 85% and made into the same form.

According to a preferred embodiment the esterification degree is comprised between 40 and 85% more preferably the esterification degree is comprised between 45 and 75%, even more preferably between 60 and 70%.

In addition the partial hyaluronic esters with benzyl alchol are to be preferred.

The biocompatible biomaterial containing the partial ester of hyaluronic acid having an esterification degree comprised in the aforementioned ranges preferably is in the form of a three dimensional matrix non woven tissue having fine fibres and/or microfibres, where "fibres" or "microfibres" signifies fibres with diameter ranging between 1 and 40 $\mu$m, preferably between 5 and 20 $\mu$m.

Another preferred biocompatible biomaterial preferably contains as hyaluronic acid derivatives the autocrosslinked esters of the aforementioned class (B).

The autocross-linked derivatives in the form of three-dimensional structures enclosing communicating hollow spaces created by pores are particularly suitable for osteochondral regeneration as they present all the abovesaid properties.

In these cases when the hollow spaces in the structure of the biomaterials containing the autocrosslinked hyaluronic acid esters are represented by communicating pores, their dimensions should vary between 10 and 700 $\mu$m with a porosity of over 80%.

The aim of the present invention is to provide biocompatible and biodegradable biomaterials containing hyaluronic acid derivatives processed in the form of three-dimensional structures enclosing communicating pores and/ or fine fibres or microfibres entangled together, with regenerative properties.

The biocompatible biomaterial for the use according to the present invention may consist essentially of said hyaluronic acid derivatives in the form of three-dimensional structures with communicating hollow spaces created by pores and/or fine fibres or microfibres entangled together, or alternatively may contain other biocompatible natural, semisynthetic or synthetic polymers.

Preferred natural polymers that can be used for this purpose, are collagen, coprecipitates of collagen and glycosaminoglycans, cellulose, polysaccharides in the form of gels such as chitin, chitosan, pectin or pectic acid, agar, agarose, xanthane, gellan, alginic acid or the alginates, polymannans or polyglycans, starch, natural gums and mixtures thereof. Preferred semisynthetic polymers are collagen cross-linked with agents such as aldehydes or precursors of the same, dicarboxylic acids or their halogenides, diamines, derivatives of cellulose, hyaluronic acid, chitin or chitosan, gellan, xanthane, pectin or pectic acid, polyglycans, polymannan, agar, agarose, natural gum, glycosaminoglycans and mixtures thereof.

Preferred synthetic polymers are polylactic acid, polyglycolic acid or copolymers of the same or their derivatives, polydioxane, polyphosphazenes, polysulphonic resins, polyurethanes, PTFE, and mixtures thereof.

The biocompatible and biodegradable biomaterials according to the present invention can contain pharmaceutically or biologically active substances such as, for example, anti-inflammatories, antibiotics, growth factors.

Said three-dimensional structures may contain inside the non-woven fabrics, cords, liophylic compositions.

The biomaterials according to the present invention can be used to advantage in human and veterinary surgery and, in particular, in plastic and aesthetic surgery, in orthopaedics, dentistry, in neurosurgery, in cardiovascular surgery, and in general as fillers for the soft tissues in cases of loss of substance.

EXAMPLE 1

Assessment of the percentage of bone regeneration in a rat model, induced by hyaluronic acid in powder form and by benzyl esters of hyaluronic acid with varying percentages of esterification, in the form of fine fibres made into the form of non-woven fabrics.

The aim of the experiment is to compare the bone regenerating properties of hyaluronic acid derivatives with various percentages of esterification made into the form of fine fibres, in turn worked into the form of non-woven fabrics.

Fifteen black and white, male rats from Lister of Liverpool, weighing between 300 and 350 g were used. The animals were anaesthetised with Immunobolin (C-Vet Ltd, Bury St Edmumds, UK) at a dose of 0.1 ml per 100 g of body weight. The area to be operated on was shaved and the skin cleansed, the femur was exposed by the cut and drain method.

A hole with a diameter of 1.76 mm was drilled in the bones of both paws under abundant irrigation with saline solution.

A periosteal support was fitted under the bone to protect the underlying muscle. Having inserted the implants in the lesion on a level with the surface of the bone, the periosteum and the soft tissue were replaced over the surface of the wound and stitched.

The outer wound was sealed with a coating of acrylic spray (Nobecutane®), Astra Pharmaceutica, Kings Langley, UK) to reduce the risk of infection. The animals were revived with Revivon® (Reckitt & Coleman) at a dose of 0.05 ml per 100 g of body weight.

The animals were treated as reported below:

| No. of animals | groups | Treatment |
| --- | --- | --- |
| 3 | 1 | HA (powder) |
| 3 | 2 | HYAFF11 (non-woven fabric) |
| 3 | 3 | HYAFF11p80 (non-woven fabric) |
| 3 | 4 | HYAFF11p65 (non-woven fabric) |
| 3 | 5 | Control |

HA: Hyaluronic acid fractions hyalastine ® and hyalectin ® (EP 0138572);
HYAFF11 (non-woven fabric): benzyl ester of hyaluronic acid with 100% esterification in the form of fine fibres worked into the form of a non-woven fabric (U.S. Pat. No. 5,520,916);
HYAFF11p65 (non-woven fabric): benzyl ester of hyaluronic acid with 65% esterification in the form of fine fibres worked into the form of a non-woven fabric (U.S. Pat. No. 5,520,916);
HYAFF11p80 (non-woven fabric): benzyl ester of hyaluronic acid with 80% esterification in the form of fine fibres worked into the form of a non-woven fabric (U.S. Pat. No. 5,520,916).

Four weeks later the animals were sacrificed by the standard method. Their femurs were removed and cut so as to separate the treated part. The bone marrow was removed by carefully injecting 40% methanol, taking care not to damage the part containing the implant.

The samples were fixed and decalcified with a Lillie solution for a minimum of three days, washed for two days in 75% alcohol, dehydrated by washing with alcohol at increasing percentages and, lastly, embedded in paraffin. The samples were then sectioned perpendicularly to the bone surface and parallel to the diameter of the defect, obtaining sections with a thickness of 7 microns.

The four most central sections of each sample were stained using haematotoxylin-eosin staining and Mallory's triple stain.

Histomorphometric assessment was performed using a microscope for image analysis (IBAS).

The percentage of bone regeneration after 24 days is shown in graph 1. As can be seen from the graph, the benzyl ester of hyaluronic acid with 65% esterification in the form of fine fibres worked into the form of a non-woven fabric induces, surprisingly a greater degree of bone regeneration than the total benzyl ester made into the same form, and hyaluronic acid in powder form.

EXAMPLE 2

Assessment of the percentage of reepithelialization in a pig model using benzyl esters of hyaluronic acid with between 65 and 100% of esterfication, in the form of fine fibres worked into the form of a non-woven fabric.

The aim of the experiment is to test in vivo the ability of two benzyl esters of hyaluronic acid with between 65 and 100% esterification to induce reepithelialization in a wound model in pig.

Six male, Yucatan micropigs of about one year old and weighing about 25–30 kg were used.

The animals were anaesthetised throughout the experiment by intramuscular injection with 8 ml of a solution containing Xilazine® (20 mg/ml) and Ketamine® (50 mg/ml) in a ratio of 1:2. Anaesthesia was boosted when necessary by intravenous injections of 5–10 mg/kg of a solution of pentobarbital at a concentration of 60 mg/ml. Each animal was shaved while under anaesthetic.

The shaved part was first washed with surgical detergent and then disinfected with an iodine solution. Six circular wounds (3 per side), measuring 4 cm in diameter were performed, completely removing both the dermal tissue and epidermal tissue while leaving the underlying muscle fascia intact.

A chamber of PTFE was placed on the wound bed using the edges of skin to fix the base of the chamber at a subcutaneous level. The chamber was closed with 2/0 silk suture sewn to the surrounding skin.

The benzyl esters of hyaluronic acid with 65% and 100% esterification in the form of fine fibres processed in the form of non-woven tissue, were applied to the wounds as shown below:

| groups | No. Of sites tested | Treatment | Dose | Administration route |
|---|---|---|---|---|
| 1 | 12 | HYAFF11p65 (non-woven fabric)** | 5 × 5 cm | Topical |
| 2 | 12 | HYAFF11 (non-woven fabric)** | 5 × 5 cm | Topical |
| 3 | 12 | — | — | — |

HYAFF11p65 (non-woven fabric): benzyl ester of hyaluronic acid with 65% esterification in the form of fine fibres worked into the form of a non-woven fabric (U.S. Pat. No. 5,520,916);
HYAFF11 (non-woven fabric): benzyl ester of hyaluronic acid with 100% esterification in the form of fine fibres worked into the form of a non-woven fabric (U.S. Pat. No. 5,520,916).
**: applications performed on the day of surgery and on the following $7^{th}$, $14^{th}$, $21^{st}$ and $28^{th}$ days.

After treatment, the wounds were covered with vaseline-soaked gauzes and the animals were wrapped in elastic bandages. In order to protect the wounds, lightweight, stiff jackets were tied round the animals' trunks.

The percentage of reepithelialization was calculated using a microscope for image analysis (IBAS).

Graph 2 shows the percentage of reepithelialization per treatment.

As can be seen from graph 2, the wounds treated with HYAFF11p65 in the form of fine fibres made into non-woven fabrics present surprisingly high reepithelialization results compared with those treated with the total ester made into the same form.

As the epithelial tissue cells could not possibly have come from either hair follicles, because the wound was a full-thickness wound, or from the edges of the wound, because they had been separated from the treatment site by the chamber of PTFE, the epithelium which formed in the presence of the test material must have originated from the progenitor cells from the wound bed recruited by the biomaterial.

EXAMPLE 3

Biomaterials in the form of three-dimensional structures enclosing hollow spaces formed by communicating pores constituted by autocross-linked derivatives of hyaluronic acid (ACP) and benzyl esters of hyaluronic acid with over 85% esterification (HYAFF1 1) in the treatment of osteochondral defects in rabbit.

The key component in the repair of fractures is the need for osteoprogenitor cells, which usually reach the lesion site by the revascularisation of the site itself, or by the migration of host progenitor cells from the periosteum and/or from the bone marrow towards the repair blastema. However, the cartilage is not a vascularised tissue, neither does it have easy access to large quantities of progenitor cells, so its repair is often unsuccessful.

The chondroprogenitor cells must possess developmental potential, they must be responsive to local cueing, they must be present in sufficient numbers, at the right density and with suitable distribution. The mesenchymal progenitor cells (MPCs) must be able to expand mitotically in vivo and to differentiate into a cartilage phenotype. Lastly, the host's biological response must support the repair of the natural, acute mechanism that requires inhibition of the natural acute inflammatory response and inhibition of revascularisation.

The mechanical environment must be controlled to support the developmental cues and regenerating tissue. This interaction between the host site and the invading chondroprogenitor cells requires an environment that supports recapitulation of embryonic events and the expansion and differentiation of chondroprogenitor cells into typical adult hyaline cartilage.

Besides the mesenchymal progenitor cells, the host site must provide the necessary signal molecules, such as, transforming growth factor $\beta 1$ to support both cell migration and their mitotic expansion, and ultimate differentiation into adult cartilage cells.

Adult joint cartilage, therefore, is poorly equipped to repair itself. The methods used to date to enhance the natural repair response do allow the regeneration of a hyaline-like cartilage, but subsequently there is a formation of varying quantities of fibrocartilage, which represents a nonfunctional repair tissue.

It has, surprisingly, been discovered that the use of hyaluronic acid derivatives facilitates the natural wound-healing response, creating an environment which is very similar to the embryonic one where the endogenous progenitor cells can regenerate damaged tissue.

The aim of this study is to test the hyaluronic acid derivatives as materials to use as implants for the treatment of osteochondral defects in rabbit.

Standard defects were created on the surface of the femoral condyle on the weight-bearing side of the bone. The defects were divided into four groups, one group received no treatment while the other three were treated with ACP biomaterial, HYAFF111 biomaterial and ACP biomaterial loaded with fresh autologous bone marrow respectively. The rabbits were sacrificed either 4 or 12 weeks after surgery and the condyles were subjected to histological analysis. The performance of the test materials was established by semi-quantitative grading of the histological sections based on a modified version of O'Driscoll's 24-point scale.

The empty, untreated defects were filled with bony tissue up to or beyond the tidemark between bone and cartilage. In these points the non-calcified top layer varied from fibrous, undifferentiated tissue to more hyaline-like tissue. None of the empty defects repaired completely.

Four weeks after surgery, the defects treated with ACP exhibited bony filling up to the tidemark between bone and cartilage and the upper layer presented well-integrated hyaline cartilage. In the 12-week specimens the cartilage was half as thick as normal cartilage.

The defects treated with HYAFF1 1 presented a rim of chondrogenic cells at the interface between the defect and the host tissue, while in the central part of the defect there was only empty, spongy tissue. The upper layer was variable but well integrated with the adjacent cartilage. At twelve weeks, most of the defects presented bony filling with a central area with or without fibrous tissue. The surfaces mostly presented hyaline-like cartilage with cracks and fissures in some cases.

The group treated with ACP loaded with bone marrow stroma presented characteristics similar to those of the group treated with ACP alone, except for the presence of a higher percentage of hyaline cartilage in the top layer at both time points.

The scores of the histological tests showed that the defects treated with ACP presented better repair than both those treated with HYAFF11 (p<0.05) and the empty, untreated ones (p<0.002). No significant differences were observed between the defects treated with HYAFF11 and the untreated ones (p=0.29).

Similarly, no significant difference was observed between the defects treated with ACP alone and those treated with ACP loaded with bone marrow stroma at four (p=0.15) and twelve weeks (p=0.06).

A preliminary pilot study was performed using four rabbits in which osteochondral defects were surgically induced in the knee. The defects were standard, measuring 3 mm in diameter and 3 mm in depth, and were performed on the surface of the femoral, load-bearing condyle. The defects were filled with the test material. The rabbits were sacrificed a week after surgery and the defects were analysed histologically to ensure that the materials were present inside them.

Thirtysix male New Zealand white rabbits were used. They were four months old and weighed 2.5 kg. Each rabbit was numbered. Defects were performed on the surface of the femoral condyle as described above and the rabbits were treated according to the following plan:

| Treatment | 4 weeks | 12 weeks |
| --- | --- | --- |
| Untreated | 12 | 12 |
| ACP | 12 | 12 |
| HYAFF11 | 6 | 6 |
| ACP + bone marrow stroma | 6 | 6 |

The defects were histologically scored with a modification of O'Driscoll's 24-point scale. The scores of both the treated and untreated defects were compared by Mann-Whitney's rank sum test. The scores attributed to the defects treated with ACP and ACP+ bone marrow stroma were compared by Wilcoxon's signed rank test. Moreover, the presence of residue tissues was assessed at two different times of sacrifice to evaluate reabsorption of the test material in the in vivo model. The bone marrow stroma with which the ACP had been loaded was obtained from the tibia of the rabbits according to the following procedure.

Experimental Procedure

Loading ACP with Bone Marrow Stroma

The rabbits were anaesthetised and the proximal medial surface of the tibia was exposed through a small incision. The subcutaneous tissue and the periosteum were incised and retracted to expose the bone surface. The tibia was perforated with a 16-gauge needle and the bone marrow stroma (4–5 ml) was aspirated from the tibial shaft with a pre-heparinised plastic tube connected to a 10-ml syringe containing 1 ml of heparin solution (3,000 units/ml).

The materials were cut into small cubes measuring 3 mm per side, which were then coated by immersion in a solution of fibronectin 100 μg/ml in Tyrode's saline solution. After an hour's incubation at 4° C., the materials were removed from the solution and left to dry overnight at room temperature.

The fresh, autologous bone marrow was incorporated in the ACP sponge in a 5-ml test tube. The tube was capped then negative pressure was applied using a 20-ml syringe fitted with a 20-gauge needle. The creation of a vacuum facilitates the exit of air bubbles in order to impregnate the material completely with bone marrow. The composition was incubated at room temperature for 20 minutes before implantation.

Surgical Procedure

The thirty-six animals were anaesthetised and the knee joints were exposed through an incision from the medial edge of the patella to the anterior edge of the distal insertion of the medial collateral ligament. The distal part of the quadriceps muscle was incised and the small vessels cauterised before incising the joint capsule. The patella was dislocated laterally and the knee maximally flexed. Osteochondral defects measuring 3 mm across and in depth were drilled at the centre of the condyle, 1.5 mm above the edge of the medial meniscus. The central area was cleared of all debris with a curette and the edges with a scalpel blade. The implant was placed in the defect, the patella reduced, the capsule and muscle were closed with double 4-0 dexon suture and the skin with a continuous 4-0 dexon suture.

Histological Process

The rabbits were sacrificed 4 and 12 weeks after surgery and the condyles were fixed in formalin, decalcified, embedded in paraffin, sectioned and stained with Toluidine blue. All the 12-week defects were scored with a modification of O'Driscoll's 24-point scale, reported hereafter:

| percentage of hyaline articular cartilage | |
| --- | --- |
| 80–100% | 8 |
| 60–80% | 6 |
| 40–60% | 4 |
| 20–40% | 2 |
| 0–20% | 0 |
| Surface regularity | |
| smooth and intact | 3 |
| Superficial horizontal lamination | 2 |
| fissures | 1 |
| severe disruption including fibrillation | 0 |
| Degenerative changes | |
| Severe hypercellularity | 1 |
| Mild or moderate hypercellularity | 2 |
| Normal cellularity, no clusters, normal staining | 3 |
| Normal cellularity, mild clusters, moderate staining | 2 |
| Mild or moderate hypocellularity, slight staining | 1 |
| Severe hypocellularity, poor or no staining | 0 |
| Structural integrity | |
| Normal | 2 |
| Slight disruption, including cysts | 1 |
| Severe disintegration | 0 |
| Thickness | |
| 121–150% of normal cartilage | 1 |
| 81–120% of normal cartilage | 2 |
| 51–80% of normal cartilage | 1 |
| 0–50% of normal cartilage | 0 |
| Integration left | |
| Bonded | 2 |
| Partially bonded | 1 |
| Not bonded | 0 |
| Integration right | |
| Bonded | 2 |
| Partially bonded | 1 |
| Not bonded | 0 |
| Bone filling | |
| 101%–125% | 2 |
| 76–100% | 3 |
| 51–75% | 2 |

-continued

| | |
|---|---|
| 26–50% | 1 |
| 0–25% | 0 |
| Tidemark | |
| Present | 1 |
| Absent | 0 |
| Degenerative changes in adjacent cartilage | |
| Normal cellularity, no clusters, normal staining | 3 |
| Normal cellularity, mild clusters, moderate staining | 2 |
| Mild or moderate hypocellularity, slight staining | 1 |
| Severe hypocellularity, poor or no staining | 0 |

Statistical Analysis

The scores of the treated defects were compared with those of the non-treated defects by the Mann Whitney rank-sum test. The scores of the defects treated with ACP and ACP+ bone marrow stroma were compared by the Wilcoxon's signed rank test.

Results

The repair tissue of the untreated defects was similar at the two observation times.

The defects presented bone tissue up to and beyond the tidemark between bone and cartilage, while the top, non-calcified layer varied from non-differentiated fibrous tissue to fibrocartilaginous tissue and tissue with more hyaline-like characteristics.

Most of the empty, untreated defects presented varying quantities of the three types of tissue, with the specimens observed at 12 weeks presenting a thinner top layer.

Four weeks after surgery, the defects treated with ACP presented a rapid endochondral bony fill up to the level of the tidemark between the bone and cartilage, except for the central part of the defect where some hypertrophic cartilage was observed. The top layer was composed of hyaline-like cartilage with impressive integration with the adjacent cartilage. The upper layer was variable. In some cases with hyaline-like cartilage and in others with fibrocartilage. At 12 weeks, most of the defects presented bony filling with a central part of fibrous tissue. Some defects revealed the presence of hypertrophic cartilage. The non-mineralised upper layer was mainly composed of hyaline cartilage, sometimes with cracks and fissures. The implant material was visible in the specimens at 4 weeks, while no residues of the material could be seen at 12 weeks.

At 4 weeks, the specimens treated with ACP+ bone marrow stroma presented the same characteristics as those treated with ACP, except for the presence of a higher percentage of hyaline cartilage in the top layer of the regeneration tissues. At 12 weeks, the overall appearance of the defects treated with ACP+ bone marrow stroma was very similar to that of the defects treated with ACP, with bony filling beyond the tidemark between bone and cartilage and a layer of cartilage tissue which was thinner than the adjacent normal cartilage. However, the non-calcified surface layer was slightly thicker in the defects treated with ACP+ bone marrow stroma, and it exhibited a staining pattern more similar to that of normal cartilage.

Integration of the regenerative tissue with the surrounding tissue was greater in the group treated with ACP+ bone marrow stroma. No residue material was found in any of the specimens.

The points scored by the samples at 12 weeks are shown below:

| Group | Score | No. |
|---|---|---|
| Non-treated | 15.5 ± 3.47 | 10 |
| ACP | 20.1 ± 3.00 | 15 |
| HYAFF11 | 17.3 ± 3.33 | 8 |

The specimens' histological scores did not show any significant differences between the defects treated with ACP and those treated with ACP+ bone marrow stroma at 4 (p=0.15) and 12 weeks (p=0.06), as reported below:

| Group | 4 weeks Score | No. | 12 weeks Score | No. |
|---|---|---|---|---|
| ACP | 16.3 ± 7.12 | 6 | 19.8 ± 3.54 | 6 |
| ACP + bone marrow stroma | 20.17 ± 5.19 | 6 | 21.2 ± 1.60 | 6 |

Conclusions

Although it is possible that different cell pools (bone marrow stroma, synoviocytes, chondrocytes) contribute to the repair process of osteochondral defects, the mesenchymal progenitor cells from the bone marrow are probably the chief contributors to the natural repair process. The natural repair tissue in the untreated defect fails to withstand the function of normal joint cartilage and degenerates in time.

A biocompatible, biodegradable, porous material to implant in the defect must have an appropriate chemical composition, must allow the differentiation of the repair cells and provide good scaffolding on which such cells can regenerate and integrate. Hyaluronic acid derivatives represent an excellent vehicle for the cells and their composition is such that they recreate an environment similar to the embryonic one that favours the regenerative process.

ACP's porous structure, moreover, presents reabsorption properties that adapt surprisingly to the dynamics of the repair processes. This study has proved that the porous biomaterial constituted by ACP per se enables osteochondral regeneration similar to that obtained with the same biomaterial loaded with bone marrow stroma.

EXAMPLE 4

Assessment of Bone Regeneration Induced by the Partial Benzyl Esters of Hyaluronic Acid with 75% Esterification (HYAFF11p75) Compared to that Induced by the Total Benzyl Esters (HYAFF11)

The aim of the study is to assess bone regeneration in bone defects created in rabbit calvaria following the implant of biomaterials constituted by hyaluronic acid derivatives.

Male, New Zealand rabbits, 8 months old and weighing about 3 kg were used. Two defects were created on the calvaria of each animal, and the animals were then treated as shown below:

| Group | No. of treatment sites | Treatment | Dose | Period of treatment in days | Route |
|---|---|---|---|---|---|
| 1 | 6 | Non-woven HYAFF11 | ≈0.15 g | 7 | Topical |
| 2 | 6 | Non-woven HYAFF11p75 | ≈0.15 g | 7 | Topical |

-continued

| Group | No. of treatment sites | Treatment | Dose | Period of treatment in days | Route |
|---|---|---|---|---|---|
| 3 | 6 | HYAFF11 powder | ≈0.15 g | 7 | Topical |
| 4 | 6 | HYAFF11p75 powder | ≈0.15 g | 7 | Topical |
| 1 | 6 | Non-woven HYAFF11 | ≈0.15 g | 10 | Topical |
| 2 | 6 | Non-woven HYAFF11p75 | ≈0.15 g | 10 | Topical |
| 3 | 6 | HYAFF11 powder | ≈0.15 g | 10 | Topical |
| 4 | 6 | HYAFF11p75 powder | ≈0.15 g | 10 | Topical |
| 1 | 6 | Non-woven HYAFF11 | ≈0.15 g | 21 | Topical |
| 2 | 6 | Non-woven HYAFF11p75 | ≈0.15 g | 21 | Topical |
| 3 | 6 | HYAFF11 powder | ≈0.15 g | 21 | Topical |
| 4 | 6 | HYAFF11p75 powder | ≈0.15 g | 21 | Topical |

Each animal was anaesthetised with an i.m. injection of 4 ml of a solution of ketamine/Xylazine, obtained by mixing 5 ml of Xylazine, 20 mg/ml and 10 ml of ketamine, 50 mg/ml. A local anaesthetic was then administered by injection to the periphery of the operation site and bone defects were performed on the calvaria, one behind and one in front of the midsagittal plane. The defects were circular in shape and measured 8 mm in diameter and 2–3 mm in depth.

After surgery, each animal was treated with antibiotics and analgesics.

The degree of bone repair was assessed at three different times after surgery: 10, 21 and 40 days, when the animals were sacrificed with carbon dioxide and the relative area of their calvarias removed.

After removal, the tissues were fixed and decalcified (about two days' treatment) with a solution composed of picric acid, formalin and formic acid. Subsequently they were embedded in paraffin and sectioned. The sections, three per specimen, were stained with haematoxylin-eosin, Mallory's triple stain and Toluidine blue or Alcian blue at pH 2.5.

The stained histological sections were analysed under a microscope for histomorphometric evaluation using a computerised morphometric system, (IBAS) based on tissue regeneration as observed from the evidence during the subsequent steps of repair expressed as a percentage of the initial dimensions of the defect.

The results reported in graph 3 show that the biomaterial constituted by the ester derivatives of hyaluronic acid with between 60% and 85% esterification (NW p75) induce a higher percentage of bone regeneration than the ester derivatives with a higher percentage of esterification (85%–100%) (NW 11) and made into the same form.

What is claimed is:

1. A method for regenerating in vivo mammal tissue comprising applying in vivo to the site requiring such a treatment a biocompatible biomaterial containing at least one hyaluronic acid derivative selected from the group consisting of esters of hyaluronic acid wherein part or all of the carboxy functions are esterified with alcohols of the aliphatic, aromatic, arylaliphatic, cycloaliphatic, heterocyclic series, said hyaluronic acid derivative being processed in the form of a three-dimensional structure enclosing hollow spaces formed by communicating pores and/or fine fibres or microfibres entangled together, wherein:

i) said biomaterial is free from cellular components and/or products thereof,
   ii) when said hyaluronic acid derivative is processed in the form of non woven tissue, it is a hyaluronic acid partial ester with benzyl and has an esterification degree of 65%.

2. The method according to claim 1, wherein said mammal tissue is human tissue selected from the group consisting of epidermal, dermal, bone, cartilage, nerve, cardiovascular, adipose and hepatic tissues.

3. The method according to claim 1, wherein said hyaluronic acid derivative is a hyaluronic acid ester with benzyl alcohol.

4. The method according to claim 1, wherein said biocompatible biomaterial consists essentially of said hyaluronic acid derivatives in the form of three-dimensional structures with communicating hollow spaces created by pores and/or fine fibres or microfibres entangled together.

5. The method according to claim 1, wherein said biocompatible biomaterial further comprises at least another biocompatible natural, semisynthetic and/or synthetic polymer.

6. The method according to claim 1, wherein said biocompatible biomaterial further contains pharmaceutically or biologically active substances.

7. The method according to claim 1, wherein said biocompatible biomaterial further contains inside the non-woven fabrics, cords and liophylic compositions.

* * * * *

UNITED STATES PATENT AND TRADEMARK OFFICE
CERTIFICATE OF CORRECTION

PATENT NO. : 6,872,819 B1
DATED : March 29, 2005
INVENTOR(S) : Alessandra Pavesio et al.

It is certified that error appears in the above-identified patent and that said Letters Patent is hereby corrected as shown below:

Title page,
Item [22], PCT Filed, should read -- May 25, 1999 --.

Signed and Sealed this

Fourteenth Day of March, 2006

JON W. DUDAS
*Director of the United States Patent and Trademark Office*